(12) United States Patent
Ziegler et al.

(10) Patent No.: US 8,036,749 B2
(45) Date of Patent: Oct. 11, 2011

(54) SYSTEM FOR CHARACTERIZING CHRONIC PHYSIOLOGICAL DATA

(75) Inventors: Paul D. Ziegler, Minneapolis, MN (US); Douglas A. Hettrick, Blaine, MN (US); Shantanu Sarkar, Saint Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 1646 days.

(21) Appl. No.: 11/096,151

(22) Filed: Mar. 31, 2005

(65) Prior Publication Data

US 2006/0224186 A1    Oct. 5, 2006

(51) Int. Cl.
*A61N 1/00* (2006.01)

(52) U.S. Cl. .......................................... 607/32; 607/60

(58) Field of Classification Search .................. 600/300, 600/519, 509, 301, 513; 607/2, 14, 19, 18, 607/515, 509, 59, 30, 32, 60; 705/3
See application file for complete search history.

(56) References Cited

U.S. PATENT DOCUMENTS

| | | | | |
|---|---|---|---|---|
| 5,309,919 A | * | 5/1994 | Snell et al. | 600/510 |
| 5,336,245 A | * | 8/1994 | Adams et al. | 607/32 |
| 5,487,754 A | * | 1/1996 | Snell et al. | 607/27 |
| 6,024,699 A | * | 2/2000 | Surwit et al. | 600/300 |
| 6,101,415 A | * | 8/2000 | Er et al. | 607/27 |
| 6,230,059 B1 | * | 5/2001 | Duffin | 607/60 |
| 6,277,072 B1 | * | 8/2001 | Bardy | 600/300 |
| 6,280,380 B1 | * | 8/2001 | Bardy | 600/300 |
| 6,312,378 B1 | * | 11/2001 | Bardy | 600/300 |
| 6,440,066 B1 | * | 8/2002 | Bardy | 600/300 |
| 6,551,252 B2 | * | 4/2003 | Sackner et al. | 600/536 |
| 2001/0051764 A1 | * | 12/2001 | Bardy | 600/300 |
| 2002/0010390 A1 | * | 1/2002 | Guice et al. | 600/300 |
| 2002/0137991 A1 | | 9/2002 | Scarantino et al. | |
| 2002/0147408 A1 | * | 10/2002 | Chen et al. | 600/513 |
| 2004/0059237 A1 | * | 3/2004 | Narayan et al. | 600/509 |
| 2004/0136556 A1 | * | 7/2004 | Litvak et al. | 381/316 |
| 2005/0080348 A1 | * | 4/2005 | Stahmann et al. | 600/529 |

OTHER PUBLICATIONS

Search Report from corresponding PCT Application Serial No. PCT/US2006/010589, dated Nov. 30, 2006 (3 pages).
Written Opinion from corresponding PCT Application Serial No. PCT/US2006/010589, dated Sep. 30, 2007 (6 pages).
International Preliminary Report on Patentability from corresponding PCT Application Serial No. PCT/US2006/010589, dated Oct. 3, 2007 (7 pages).
European Communication from corresponding European Patent Application No. 06 739 403.1-1265 dated Feb. 5, 2008 (3 pages).
Reply to European Communication from corresponding European Patent Application No. 06 739 403.1-1265 dated May 14, 2008 (8 pages).
European Search Report, EP Application No. 06739403.1, dated Aug. 19, 2009, 3 pages.

* cited by examiner

*Primary Examiner* — Carl H Layno
*Assistant Examiner* — Roland Dinga

(57) ABSTRACT

An implantable medical device (IMD) senses physiological episodes and stores data associated with the physiological episodes in the IMD. The data is then processed based on a pattern of recurrence of the physiological episodes.

18 Claims, 5 Drawing Sheets

SYSTEM FOR CHARACTERIZING CHRONIC PHYSIOLOGICAL DATA

BACKGROUND OF THE INVENTION

The present invention relates to implantable medical devices. More particularly, the present invention relates to processing chronic physiological data from an implantable medical device (IMD) based on patterns of recurrence in the physiological data.

An important aspect of modern health care is the need to monitor the vital signs and other medical episodes and data associated with a patient, particularly those who have an IMD to treat an illness or medical condition. This monitoring has traditionally been performed by having a patient visit a hospital or clinic so that a programmer or a similar device can interrogate the IMD to gather and display the information that the IMD has stored.

Recent developments in monitoring technology have made it possible for a patient to upload data from an IMD to a remote location via a communication network such as the worldwide web, using a telephone connection or a similar type of connection to transmit the information from the IMD to the remote location. One system for this type of communication is the CareLink® network provided by Medtronic, Inc. of Minneapolis, Minn. The remote monitoring provided by such systems allows a patient with an IMD to reduce the number and frequency of visits to a hospital or clinic, by periodically uploading data for review by a physician or other medical personnel to determine whether further follow up analysis is necessary. This capability gives patients significantly greater freedom in their lifestyle, and has brought a higher quality of life to many patients.

For data that is best characterized by temporal patterns or information (e.g., atrial arrhythmia burden data), the timing of scheduled reporting of data may fail to accurately characterize the data if it has a period of repetition longer than the reporting interval. In these cases, diagnostic parameters extracted from the data may differ significantly from the true value of the parameters. In addition, it is possible that more long-term patterns of variability will not be observed if changes in the temporal patterns are not monitored. For example, a change in a patient's condition may not be observed if the clinician is unable to properly characterize the data provided by the IMD. Furthermore, resources in the IMD (e.g., memory) may be used inefficiently if temporal information in the data is not taken into consideration when processing data.

BRIEF SUMMARY OF THE INVENTION

The present invention is an implantable medical device (IMD) that senses physiological episodes and stores data associated with the physiological episodes in the IMD. The data is then processed based on a pattern of recurrence of the physiological episodes.

DETAILED DESCRIPTION

Figure 1:
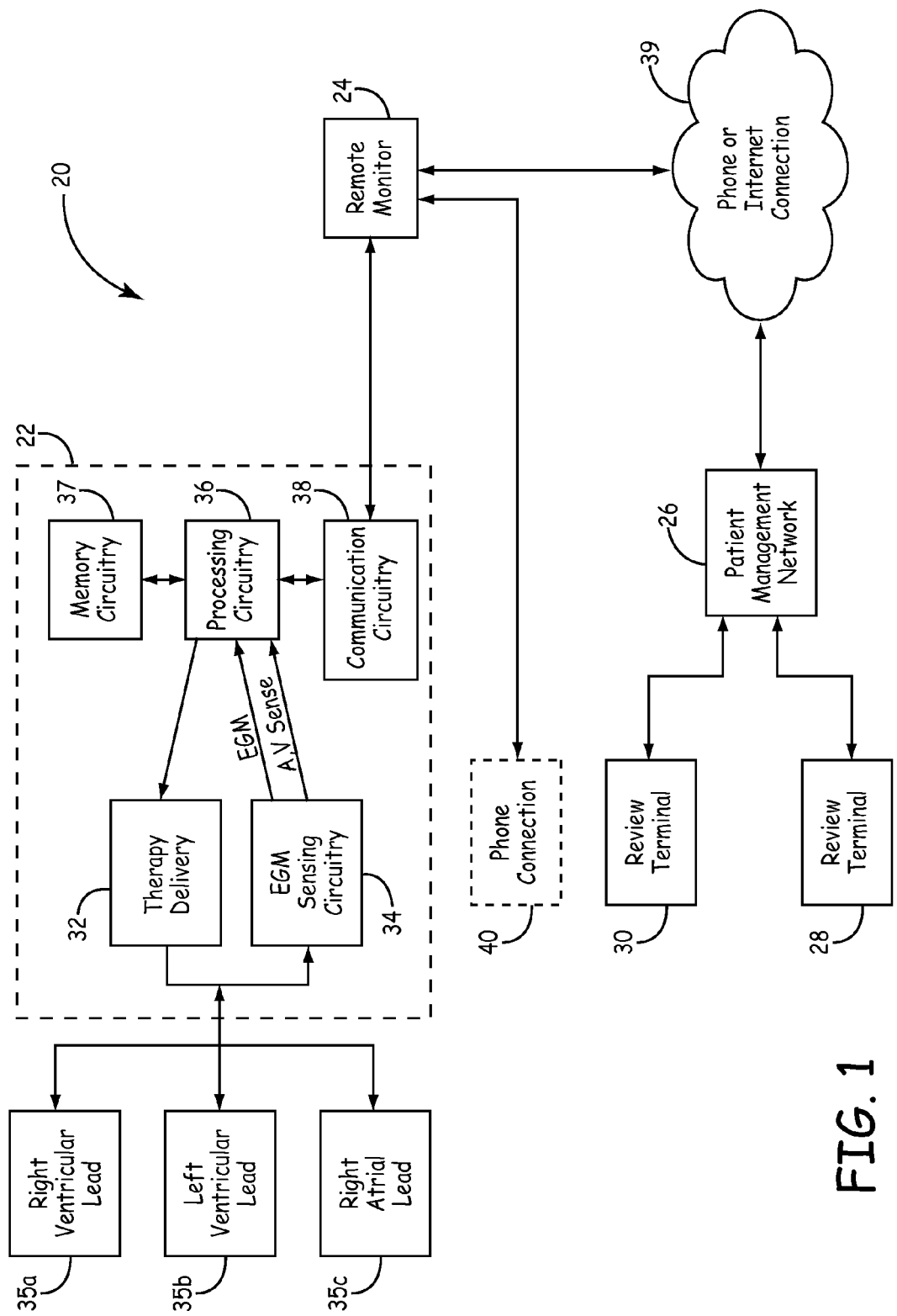
FIG. 1 is a schematic representation of a cardiac rhythm management system.

FIG. 1 is a schematic representation of cardiac rhythm management system 20, which includes implantable medical device (IMD) 22, remote monitor 24, patient management network 26, and review terminals 28 and 30. IMD 22 may be a pacemaker, defibrillator, cardioverter, pacemaker/cardioverter/defibrillator (PCD), heart function monitor having pacing capabilities, or other implantable device that includes the capability of providing therapy to a patient's heart. In addition, IMD 22 may be a device employed for continuously monitoring a patient's heart, such as the Reveal® Insertable Loop Recorder sold by Medtronic, Inc. of Minneapolis, Minn. IMD 22 may include therapy delivery circuitry 32 and electrogram (EGM) sensing circuitry 34, both operatively connected to right ventricular lead 35a, left ventricular lead 35b, and right atrial lead 35c. Therapy delivery circuitry 32 and sensing circuitry 34 are controlled by processing circuitry 36. Memory circuitry 37 is provided for storing sensed data. IMD 22 communicates externally with communications circuitry 38 that communicates information wirelessly via telemetry.

Leads 35a, 35b, and 35c are positioned to provide pacing or defibrillation pulses and sense electrical activity at desired locations in or on the patient's heart. It will be recognized by those skilled in the art that electrode assemblies can be positioned at various locations that depend upon the type of therapy provided to the patient. Each lead 35a, 35b, and 35c can include multiple sense/pace electrodes, as well as defibrillation coil electrodes. EGM data is sensed by measuring voltage differentials between any pair of EGM sensing electrodes (e.g., tip-to-coil, tip-to-ring, and tip-to-can EGM sensing).

Remote monitor 24 is a computer or programmer that communicates with IMD 22 by telemetry, or through other wireless means and is connected to patient management network 26 by phone or Internet connection 39. Remote monitor 24 is typically located in the patient's home, and can interrogate IMD 22. For instance, remote monitor 24 can initiate testing of IMD 22 at night, while the patient is sleeping, without any direct activation by the patient. An optional phone connection 40 can be provided with remote monitor 24 for communicating with a technician or clinician (e.g., via a "help line" or similar support system).

Patient management network 26 can include an Internet-accessible server that is connected (through a local area network, the Internet, etc.) to computers that function as review terminals 28 and 30. Data from IMD 22 can be transmitted to patient management network 26 via remote monitor 24, and can be stored in a database on network 26. Terminals 28 and 30 permit patients, healthcare providers, and technicians to access patient data to monitor arrhythmia data on a substantially real-time basis, for example.

A description of right ventricular lead 35a and left ventricular lead 35b is omitted for clarity, as an understanding of their function is not needed for an understanding of the present invention. Ventricular leads 35a and 35b are shown only for purposes of illustrating their connectivity with IMD 22.

In operation, leads 35a, 35b, and 35c provide therapy to a patient and sense activations that occur during cardiac episodes. For example, right atrial lead 35c senses atrial activations that may occur during episodes of atrial arrhythmia, such as atrial tachycardia (AT) and atrial fibrillation (AF). Right atrial lead 35c is electrically coupled to EGM sensing circuitry 34. EGM sensing circuitry 34 continually monitors for episodes of atrial arrhythmia and produces chronic data associated with the episodes of atrial arrhythmia. The chronic data is stored in memory circuitry 37. The chronic data stored in IMD 22 may be related to the arrhythmia burden (i.e., how much time out of a day is spent in a state of arrhythmia) and to the frequency of occurrence of arrhythmia episodes.

Periodically, IMD 22 is interrogated to report the chronic data stored in the memory circuitry of IMD 22 for analysis. Remote monitor 24 may be a programmer at a clinician's office or a remote device for uploading data via a communications network, such as the worldwide web. IMD 22 includes communication circuitry 38 that communicates information wirelessly with remote monitor 24 via telemetry signals. Upon interrogation, IMD 22 transmits information to remote monitor 24 relating to the operation of EGM sensing circuitry 34, such as diagnostic information, sensed conditions associated with the patient (including the chronic data relating to the arrhythmia burden and to the frequency of occurrence of arrhythmia episodes), or any other information collected or identified by IMD 22.

Figure 2A:
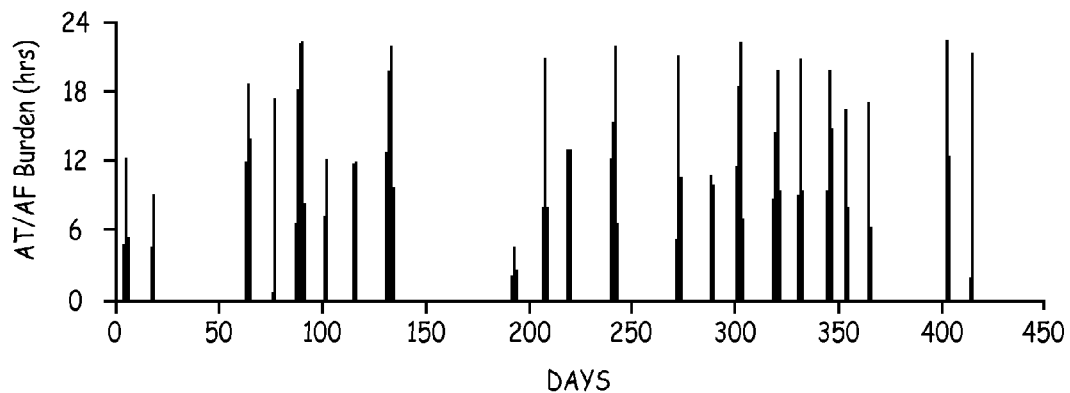
FIGS. 2A and 2B are bar graphs showing atrial arrhythmia burden data over an extended period of time for two different patients.
Figure 2B:
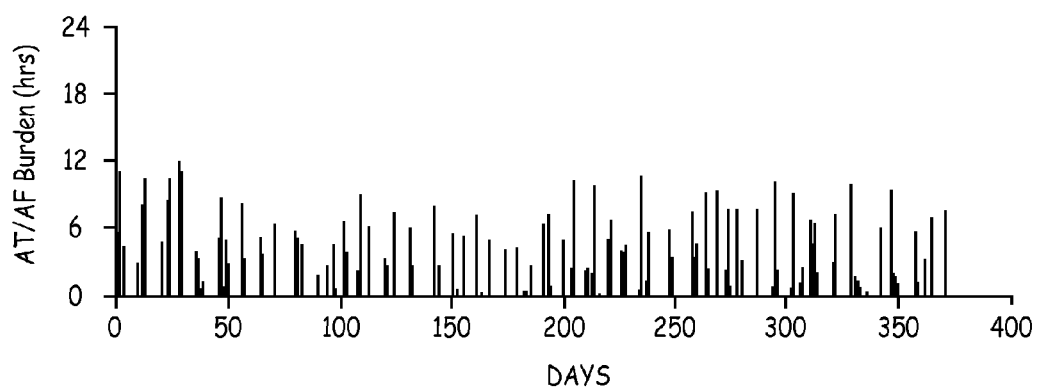

When data is best characterized by temporal patterns (e.g., atrial arrhythmia burden data), the timing of the scheduled reporting may fail to accurately characterize the data if it has a period of repetition longer than the reporting interval. To illustrate, FIGS. 2A and 2B show bar graphs of total atrial arrhythmia burden (that is, how much time out of a day is spent in a state of atrial tachycardia or atrial fibrillation) obtained from PCDs implanted in patients A and B, respectively. The atrial arrhythmia burden in each patient was measured over an extended period of time (approximately one year). Patient A experienced episodes of atrial arrhythmia less frequently than Patient B (that is, the percentage of time in atrial arrhythmia was less for Patient A), but the overall burden of each episode was more significant for Patient A than for Patient B. Due to the differences in frequency of occurrence of the arrhythmia episodes between Patient A and Patient B, an appropriate interval for reporting data stored in IMD 22 is not the same for Patient A and Patient B. In other words, if the same reporting interval is used for Patient A and Patient B (e.g., weekly), the chronic data reported by each patient may fail to accurately characterize short- and long-term patterns of repetition and variability within the data. As a result, the chronic data reported for a particular reporting interval may fall between episodes of atrial arrhythmia.

In an embodiment of the present invention, the chronic data is adaptively reported for analysis and diagnosis based on a pattern or cycle of recurrence of physiological episodes or events. For example, an appropriate interval for presenting the chronic data may be determined by establishing the dominant frequency of repetition for the chronic data. One approach to determining the dominant frequency of repetition for the data is by performing a fast Fourier transform (FFT) on the data. An FFT is a simplified form of a discrete Fourier transform, which converts time domain data into frequency domain data. The simplified algorithm uses less processing resources than the more complex discrete Fourier transform. This is because the FFT requires only $2N \log N$ calculations, while a discrete Fourier transform requires $2N^2$ calculations (where N is the number of discrete time samples).

Figure 3A:
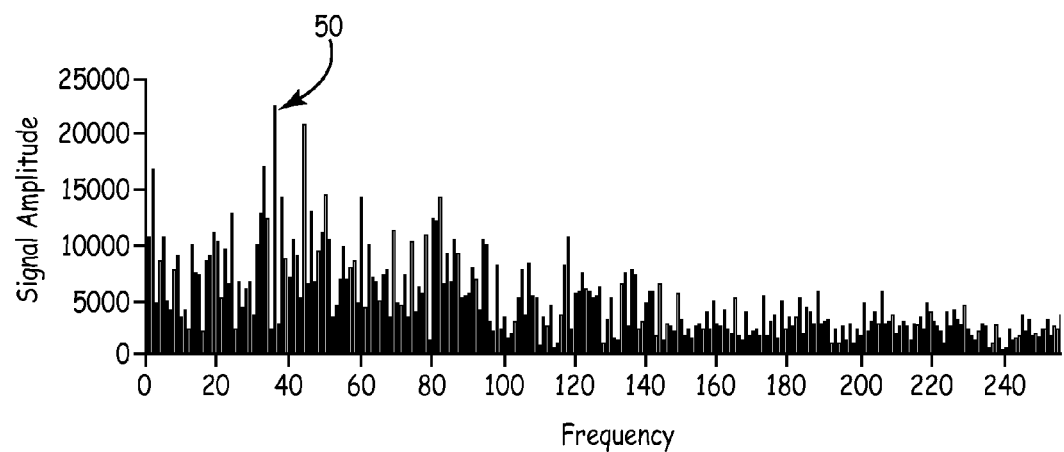
FIG. 3A is a bar graph showing the results of a fast Fourier transform (FFT) on the atrial arrhythmia burden data shown in FIG. 2A.
Figure 3B:
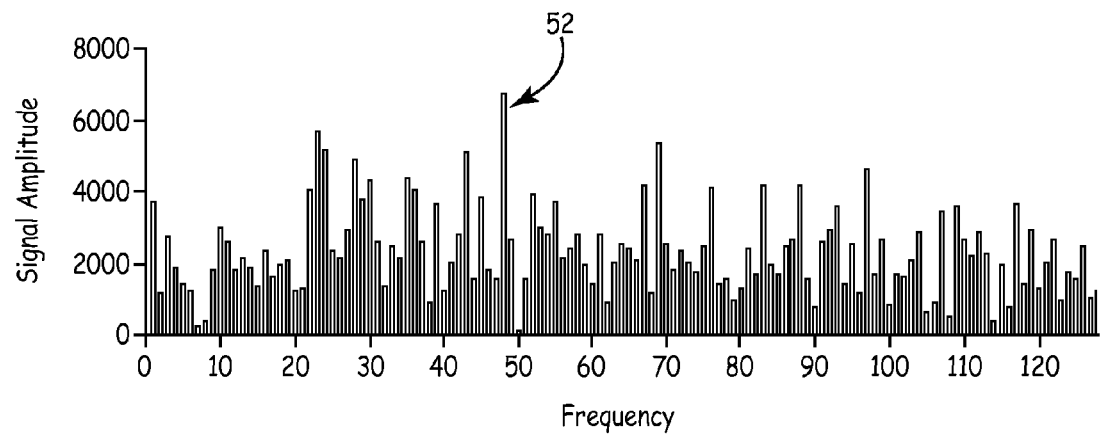
FIG. 3B is a bar graph showing the results of a fast Fourier transform (FFT) on the atrial arrhythmia burden data shown in FIG. 2B.

FIGS. 3A and 3B show bar graphs of FFTs performed on chronic atrial arrhythmia data for Patient A (FIG. 2A) and Patient B (FIG. 2B), respectively. The dominant frequency (or period) of repetition can be extracted from the graph by manipulating the frequency component with the highest amplitude. For Patient A, the highest amplitude occurs at frequency component 50 (which is at a frequency of 36/day). Based on the number of samples taken, this translates to a dominant period of repetition of 14.2 days. For Patient B, the highest amplitude occurs at frequency component 52 (which is at a frequency of 48/day). Based on the number of samples taken, this translates to a dominant period of repetition of 5.3 days. Thus, if both Patients A and B are required to provide data stored in their respective IMDs on a weekly basis, for example, the data provided by Patient B will more likely be representative of the underlying temporal patterns than the data provided by Patient A.

Once the dominant frequency or period of repetition has been determined for the chronic data, the health care provider in charge of analyzing the data and programming IMD 22 may change the interval for reporting the chronic data to assure that the chronic data reported characterizes the underlying temporal patterns. In one embodiment, the reporting interval is a multiple of the dominant period of repetition of the chronic data. When the chronic data is reported at intervals based on the dominant period of repetition of the chronic data, clinical decisions regarding programming the IMD for therapy are more likely to be in agreement with the underlying condition being treated. In the case of the chronic atrial arrhythmia burden data, the clinician is more likely to know the extent of the burden in both Patient A and Patient B (and the effects therapy has on the arrhythmia) if the interval for reporting the chronic data is based on the dominant period of repetition of the chronic data. As a result, the clinician can classify the patient's burden extent and can reprogram IMD 22 as necessary to deliver appropriate therapies.

The temporal patterns or cycles of many physiological events or episodes (including atrial arrhythmia burden) have a tendency to fluctuate over time as administered therapies either treat or fail to treat the underlying physiological condition. In the latter case, these fluctuations may be indicative of an underlying change in the condition or progression of the disease being treated, which may necessitate medical intervention (such as a change in therapy delivered). In addition, other physiological conditions in the patient may impact the temporal patterns of the physiological condition being treated. Consequently, an appropriate reporting interval for a particular patient will change as the physiological condition changes. The present invention overcomes these potential errors by accounting for these changes through adaptively varying the interval for reporting chronic data to assure that the reported data correctly represents the temporal patterns in the chronic data. In particular, each time chronic data from IMD 22 is reported to remote monitor 24, remote monitor 24 determines whether the dominant frequency of repetition of the chronic data has changed since the previous reporting period. If the dominant frequency of repetition of the chronic data has changed, a new reporting interval is established based on the new dominant frequency of repetition (either by the health care provider or automatically by remote monitor 24).

In an alternative embodiment, processing circuitry 36 of IMD 22 continually updates the dominant frequency of repetition of the chronic data stored in memory circuitry 37. For example, as chronic data is sensed and stored in IMD 22, processing circuitry 36 periodically performs an FFT on the stored data to continually reestablish the dominant frequency of repetition of the data. IMD 22 may be programmed to adaptively transmit data (or alert the patient when a transmission is appropriate) at intervals based on the dynamically updated dominant frequency of repetition. In addition, IMD 22 may be programmed to alert the patient or clinician when a change in the dominant frequency of repetition occurs, which may be indicative of a change in the underlying physiological condition being treated. For example, if the change in the dominant frequency of repetition is indicative of a deteriorating physiological condition, IMD 22 may be programmed to emit an audible alarm relating to the extent of the change in condition or indicating that a different treatment strategy may need to be employed. Likewise, if the change in the dominant frequency of repetition is indicative of an improvement in the underlying physiological condition, IMD 22 may be programmed to alert the patient or clinician more passively (e.g., by emitting a signal to remote unit 24).

Besides establishing an appropriate reporting interval for the chronic data, the chronic data may also be characterized to optimize the operation of IMD 22. That is, remote monitor 24 may adjust settings or programming parameters in IMD 22, or IMD 22 may do so automatically, based on the characterized chronic data. In one embodiment, use of memory circuitry 37 in IMD 22 is optimized by adjusting the resolution of data stored by memory circuitry 37 based on recurrence patterns in the data. For example, in a patient having infrequently occurring physiological episodes, the available memory in memory circuitry 37 is allocated to record a large amount of detail for each episode. In contrast, in a patient having frequently occurring physiological episodes, IMD 22 is more selective in allocation of memory circuitry 37 since data for more events must be stored. In this embodiment, when IMD 22 reports chronic data, memory circuitry 37 preferably has a minimal amount of unused space (e.g., one byte).

In addition to assuring that chronic data obtained from IMD 22 accurately characterizes patterns or cycles of repetition in the data, it is also important to be able to characterize the chronic data in terms of long-term patterns based on the frequency and duration of recurrence of the physiological condition. In another embodiment of the present invention, chronic data from IMDs in a large sampling of patients is categorized based on temporal patterns in the data. A clinician may use this categorization to determine an appropriate interval for reporting of the chronic data, to more accurately characterize and diagnose the underlying condition, and to administer an appropriate therapy regimen.

Figure 4:
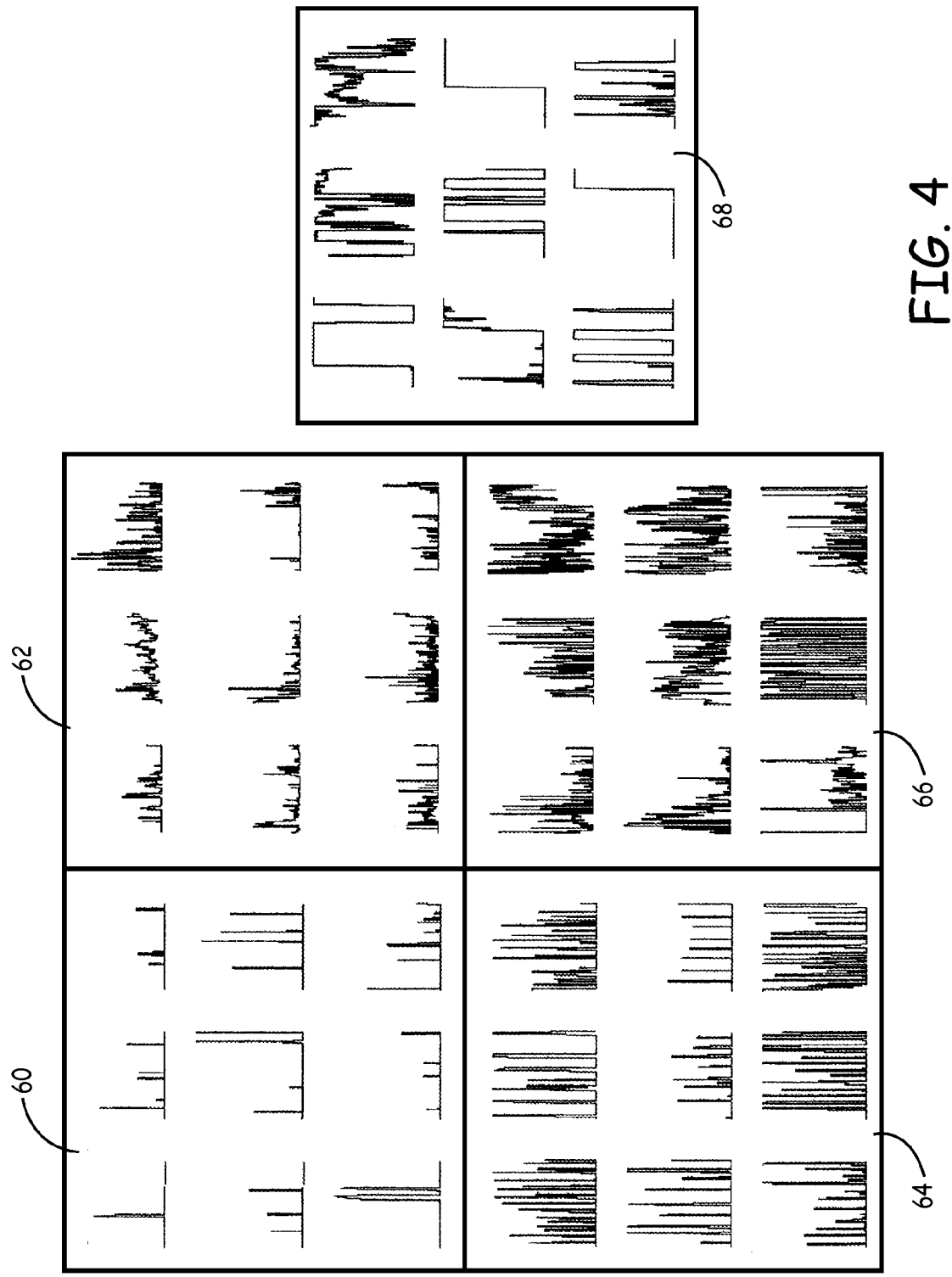
FIG. 4 is a diagram that categorizes paroxysmal atrial arrhythmia burden data from a group of patients into related categories of data.
Figure 5:
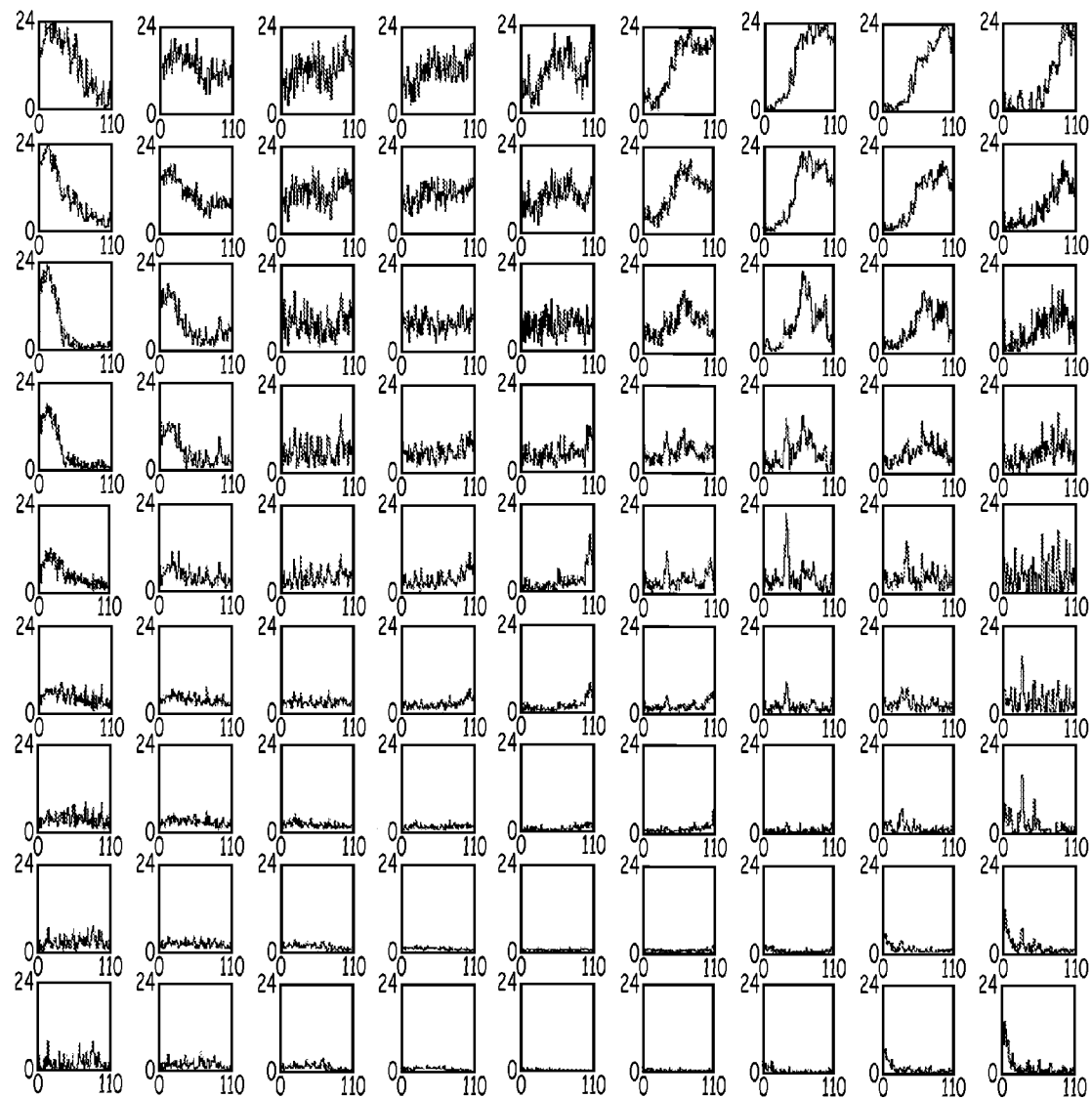
FIG. 5 shows a self-organizing map (SOM) including category models constructed from atrial arrhythmia burden data from a large number of patients.

FIG. 4 shows another embodiment of the present invention, showing a diagram that categorizes paroxysmal and persistent atrial arrhythmia burden patterns from a sampling of patients using a self-organizing map (SOM). For a thorough explanation of self-organizing maps, see Kohonen, T. (1995), *Self-Organizing Maps*, Series in Information Sciences, Vol. 30, Springer, Heidelberg, 2nd Ed. (1997). In short, an SOM constructs category models from a large collection of data, such as chronic data from a large number of patients. To illustrate, FIG. 5 shows an example SOM including a nine-by-nine arrangement of category models constructed from atrial arrhythmia burden data from a large database of patient data. The category models are arranged such that neighboring category models in the SOM have similar characteristics. The SOM in FIG. 5 is used to organize chronic data from the sampling of patients into the categories shown in FIG. 4 based on the category models. The criteria for each category model changes dynamically as data from more patients is integrated into the database.

In the embodiment shown in FIG. 4, four categories of paroxysmal atrial arrhythmia are identified (categories 60, 62, 64, and 66), and one category of persistent atrial arrhythmia is identified (category 68) from the sampling of patients based on the category models in FIG. 5. Paroxysmal atrial arrhythmia is a sporadic arrhythmia that is characterized by an abrupt onset and termination of arrhythmia episodes. Persistent atrial arrhythmia is an arrhythmia that is characterized by episodes of continuous burden for several days (typically more than seven). The burden data in FIG. 4 was collected by measuring the total burden for a day in each patient for a period of 120 days. Each category 60-68 categorizes the atrial arrhythmia burden data based on their daily burden patterns. This categorization is performed either manually by a health care provider with the aid of visual representations of the category models in the SOM or automatically by quantitative analysis of the data relative to the SOM. Category 60 includes patients having daily burden that occurs occasionally over time, category 62 includes patients having small daily burden occurring consistently almost every day, category 64 includes patients having large daily burden occurring frequently over time, and category 66 includes patients having large daily burden occurring consistently everyday. In another embodiment, the categories in the SOM are determined based on the frequency of atrial arrhythmia episodes. In a further embodiment, the categories in the SOM are determined based on a combination of the daily burden and episode frequency.

The diagram shown in FIG. 4 may be produced from an SOM by organizing chronic data from a group of patients into categories based on temporal patterns in the data, attributes of temporal patterns (e.g., mean, coefficient of variation, dominant frequency, etc.), or other attributes (e.g., patient demographics, therapy regimen, etc.). When chronic data from a group of patients has been categorized using an SOM or a neural network technique, the categories may be presented to a clinician for analysis. In one embodiment, the chronic data from a group of patients is stored in patient management network 26 and is categorized for analysis and display on review terminals 28 and 30.

While four categories are shown in FIG. 4, any number of categories may be included in the diagram in accordance with the present invention. In addition, while the exemplary embodiment describes the use of an SOM to organize the chronic data, other data processing techniques (such as supervised or unsupervised neural networks, k-means clustering, principal component analysis, independent component analysis, and decision trees) may also be used to arrive at a similar categorization system.

Once an SOM of data has been established, a clinician may correlate chronic data for individual patients with one of the categories derived from the category models in the SOM. This may provide the clinician with a guideline for determining an appropriate reporting interval for the chronic data stored in IMD 22. For example, the clinician may assign a reporting interval to each category that accurately characterizes the data in that category. Thus, when a patient's chronic data is incorporated into the proper category, a reporting interval that is appropriate for that patient's data is immediately known.

In addition, the category in which the chronic data is placed may provide the clinician with a guideline for diagnosis of the underlying condition or for prescribing an appropriate therapy based on the categorization. That is, the clinician may associate certain categories with particular therapies that are effective with patients whose data falls within that category. For example, a clinician may determine that patients whose chronic data is categorized in category 60 and 64 have arrhythmias that are more likely due to focal triggers, and thus respond well to pulmonary vein isolation. Thus, if a patient's chronic data falls into or moves to categories 60 or 64, then pulmonary vein isolation is likely the best therapy for that patient.

If a patient's condition changes such that a change in the categorization of the patient's chronic data occurs, the chronic data is adaptively categorized in the appropriate category. For example, in the embodiment shown in FIG. 4, a patient's daily burden may change from occurring occasionally over time to a small daily burden occurring consistently almost every day (necessitating a change from category 60 to 62). This may be indicative of a change in the underlying condition being treated, and a corresponding change in therapy may be necessary. Since different reporting intervals are assigned to each category, this would also result in a change in the reporting interval for that patient.

In summary, for chronic data that is best characterized by temporal patterns, diagnostic parameters extracted from the data may differ significantly from the true value of the parameters and long-term patterns of variability may not be observable. The present invention is a system and method for processing chronic data collected by an implantable medical device (IMD) based on a pattern of recurrence of physiological episodes. The IMD continually senses physiological episodes and stores data associated with the physiological episodes in the IMD. The data is then processed based on a pattern of recurrence of the physiological episodes.

Although the present invention has been described with reference to preferred embodiments, workers skilled in the art will recognize that changes may be made in form and detail without departing from the spirit and scope of the invention. For example, while the embodiments described have been directed to the characterization of atrial arrhythmia burden data, the present invention may be applied to chronic data associated with the treatment of other physiological conditions, such as congestive heart failure. The present invention may also be applied to any type of chronic physiological data that is characterizable based on temporal patterns in the data (e.g., hemodynamic changes, patient activity, heart rate at day and night, heart rate variability, systolic, diastolic, and pulse pressure, etc.). The characterized chronic data may then be reported based on patterns of recurrence or repetition in the data. Also, changes in the data may be monitored and analyzed to determine whether they are related to a change in the underlying condition being treated. Further, the device may be reprogrammed to alter the therapy delivered by the medical device.

In addition, all embodiments described have been directed to chronic data produced by IMD 22, a pacemaker/cardioverter/defibrillator (PCD). It will be appreciated that the present invention is not limited to the management of chronic data produced by a PCD. The methods of the present invention are applicable to any type of IMD including, but not limited to, a cardiac pacemaker, a defibrillator, a muscular stimulator, a brain stimulator, a nerve stimulator, a drug delivery device, an implantable loop recorder, or a physiological monitor. In essence, any device that produces chronic data that is characterizable based on temporal patterns may be used in accordance with the present invention.

Furthermore, other signal processing algorithms and techniques may be employed to characterize the chronic data based on temporal patterns. For example, the coefficient of variation of the chronic data (i.e., the average divided by the standard deviation of the data) may be determined to establish the repeatability of the data. More specifically, a lower coefficient of variation for a set of chronic data indicates that the patient's physiological episodes occur more frequently or consistently, while a higher coefficient of variation indicates that the patient's physiological episodes occur less frequently or consistently. Consequently, the coefficient of variation may be used to adaptively determine an appropriate reporting interval for the chronic data. In addition, changes in the coefficient of variation may be indicative of a change in the underlying condition being treated, which may require a change in the therapy administered by the device.

The invention claimed is:

1. A method for processing data from an implantable medical device (IMD), the method comprising:
   sensing physiological episodes;
   storing data associated with the physiological episodes in the IMD; and
   reporting the stored data on a schedule that is based on a pattern of recurrence of the physiological episodes, wherein reporting the data on the schedule that is based on the pattern of recurrence of the physiological episodes comprises:
   determining a dominant frequency of repetition of the physiological episodes; and
   establishing the schedule for transmission of the data based on a multiple of the dominant frequency of repetition of the physiological episodes.

2. The method of claim 1, and further comprising providing an output based on the pattern of recurrence of the physiological episodes.

3. The method of claim 2, wherein providing an output based on the pattern of recurrence of the physiological episodes comprises reporting a change in the pattern of recurrence of the physiological episodes.

4. The method of claim 2, wherein providing an output based on the pattern of recurrence of the physiological episodes comprises administering therapy based on pattern of recurrence of the physiological episodes.

5. The method of claim 1, wherein determining a dominant frequency of repetition of the physiological episodes comprises performing a fast Fourier transform (FFT) on the data.

6. The method of claim 1, further comprising modifying settings in the IMD based on the pattern of recurrence of the physiological episodes.

7. The method of claim 6, wherein modifying settings in the IMD based on the pattern of recurrence of the physiological episodes comprises adjusting therapy administered by the IMD based on the pattern of recurrence of the physiological episodes.

8. The method of claim 6, wherein modifying settings in the IMD based on the pattern of recurrence of the physiological episodes comprises adjusting a resolution of data stored in the IMD based on the pattern of recurrence of the physiological episodes.

9. The method of claim 1, further comprising categorizing the data based on a frequency and duration of recurrence of the physiological episodes.

10. The method of claim 1, further comprising adaptively varying the schedule based on the pattern of recurrence of the physiological episodes.

11. The method of claim 1, further comprising determining whether the pattern of recurrence of the physiological episodes has changed since a prior reporting period, and generating an alert when a change in the pattern of recurrence occurs.

12. The method of claim 1, wherein the physiological episodes comprise arrhythmia episodes.

13. The method of claim 12, wherein the data comprises information relating to a frequency of occurrence of arrhythmia episodes.

14. The method of claim 1, wherein the data comprises information relating to an arrhythmia burden.

15. The method of claim 1, wherein the schedule is predetermined.

16. A method for processing data from an implantable medical device (IMD), the method comprising:
   sensing physiological episodes;
   storing data associated with the physiological episodes in the IMD;
   reporting the stored data on a schedule that is based on a pattern of recurrence of the physiological episodes; and
   modifying settings in the IMD based on the pattern of recurrence of the physiological episodes, wherein said modifying settings in the IMD comprises adjusting a resolution of data stored in the IMD based on the pattern of recurrence of the physiological episodes.

17. A method for processing data from an implantable medical device (IMD), the method comprising:
   sensing physiological episodes;
   storing data associated with the physiological episodes in the IMD;
   reporting the stored data on a schedule that is based on a pattern of recurrence of the physiological episodes; and
   determining whether the pattern of recurrence of the physiological episodes has changed since a prior reporting period, and generating an alert when a change in the pattern of recurrence occurs.

18. A method for processing data from an implantable medical device (IMD), the method comprising:
   sensing physiological episodes;
   storing data associated with the physiological episodes in the IMD;
   detecting or determining a pattern of recurrence of the physiological episodes; and
   reporting the stored data on a schedule that is based on the detected or determined pattern of recurrence of the physiological episodes.

* * * * *